United States Patent [19]

Chen et al.

[11] Patent Number: 5,104,637

[45] Date of Patent: Apr. 14, 1992

[54] RADIO LABELED DIHEMATOPHORPHYRIN ETHER AND ITS USE IN DETECTING AND TREATING NEOPLASTIC TISSUE

[75] Inventors: I. Wen Chen, Cincinnati; Harry R. Maxon, III, Terrace Park; Jack Gluckman, Cincinnati, all of Ohio

[73] Assignee: University of Cincinnati, Cincinnati, Ohio

[21] Appl. No.: 698,565

[22] Filed: Feb. 6, 1985

[51] Int. Cl.$^5$ ................. A61K 49/02; A61K 43/00
[52] U.S. Cl. ................................. 424/1.1; 424/9; 540/145
[58] Field of Search ............ 424/1.1, 9; 128/1.1, 128/654, 659; 260/245.91; 252/645; 540/145; 600/1, 3

[56] References Cited

U.S. PATENT DOCUMENTS

| | | | |
|---|---|---|---|
| 3,855,208 | 12/1974 | Rutner et al. | 424/1.1 |
| 3,925,355 | 12/1975 | Piasio et al. | 424/1.1 |
| 3,954,739 | 5/1976 | Wilkinson | 424/1.1 |
| 4,460,559 | 7/1984 | Goldenberg | 424/1.1 |
| 4,485,086 | 11/1984 | Wong | 424/1.1 |
| 4,500,507 | 2/1985 | Wong | 424/1.1 |
| 4,500,508 | 2/1985 | Srivastave et al. | 424/1.1 |
| 4,541,438 | 9/1985 | Parker et al. | 424/9 |
| 4,571,332 | 2/1986 | Schroit et al. | 424/1.1 |
| 4,577,636 | 3/1986 | Spears | 128/654 |
| 4,649,151 | 3/1987 | Dougherty et al. | 540/145 |
| 4,877,872 | 10/1989 | Morgan et al. | 540/145 |

FOREIGN PATENT DOCUMENTS 1173828 9/1984 Canada .

OTHER PUBLICATIONS

Maxon, III et al., *Endocrinology and Metabolism Clinincs of N. America*, vol. 19, No. 3, pp. 685-715 (1990).
Kaplan et al. (Kaplan), "Monoclonal Human Antibodies: A Recent Development with Wide-Ranging Clinical Potential", in McMichael et al. (editor), *Monoclonal Antibodies in Clinical Medicine*, New York, Academic Press, Chap. 2, pp. 17-35 (1982).
PCT Application No. PCT/US83/013179; Oncology Research & Development, Purified Hematoporphyrin Derivative for Diagnosis and Treatment of Tumors and Method.
P. Fraker & J. Speck, Jr., Protein and Cell Membrane Iodinations with a Spraingly Soluble Chloroamide, 1,3,4,6-Tetrachloro-3a,6a-Diphenylclycoluril; vol. 80, No. 4, 1978, Biochemical & Biophysical Research Communications; ppl. 849-857.
T. Dougherty, W. Potter & K. Weishaupt; The Structure of the Active Component of Hematoporphyrin Derivative; Porphyrins in Tumor Phototherapy, ed. 1984, pp. 23-35.
D. Wong, A Simple and Efficient Method of Labelling Hematoporphyrin Derivative with $^{111}$In; Int. J. Appl. Radiat. Iso. vol. 35, No. 7, pp. 691-692, 1984.
D. Wong, A. Mandal, I. Reese, J. Brown & R. Siegler,
In Vivo Assessment of $^{99m}$Tc-Labeled Hematoporphyrin Derivative in Tumor Bearing Animals, Int. J. Nucl. Med. Biol., vol. 10, No. 4, pp. 211-218, 1983.
C. Gomer & T. Dougherty, Determination of [$^3$H]-and [$^{14}$C] Hematoporphyrin Derivative Distribution in Malignant and Normal Tissue; Cancer Research 39, 146-151, Jan. 1979.
R. Thaller, D. Lyster, & D. Dolphin; Potential Use of Radiolabelled Porphyrins for Tumor Scanning; Univ. of British Columbia.

*Primary Examiner*—Robert L. Stoll
*Assistant Examiner*—John M. Covert
*Attorney, Agent, or Firm*—Wood, Herron & Evans

[57] ABSTRACT

Radiolabeled dihematoporphyrin ether having the following general formula

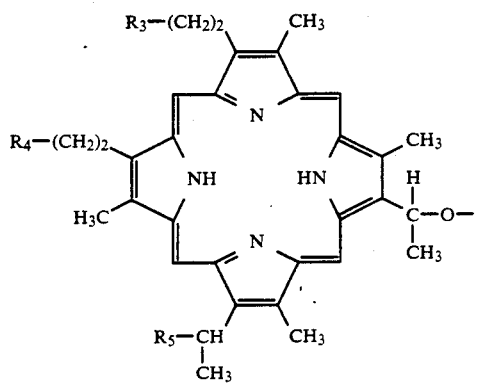

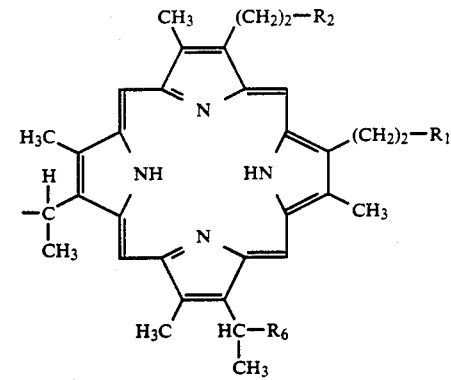

wherein at least one of $R_1$–$R_6$ is a moiety labeled with a radionuclide imaging agent is useful in providing a noninvasive nuclear scintillation image. This dihematoporphyrin ether localizes in neoplastic tissue and thus provides a method of imaging and recording the location of neoplastic tissue. When the labeling agent has an adequate component of particulate radiation, the dihematoporphyrin ether can be used as a therapeutic agent as well as a diagnostic imaging agent.

6 Claims, No Drawings

RADIO LABELED DIHEMATOPHORPHYRIN ETHER AND ITS USE IN DETECTING AND TREATING NEOPLASTIC TISSUE

BACKGROUND OF THE INVENTION

Early detection of malignant neoplastic tissue is absolutely critical for successful treatment of many types of cancer. Various methods have been used to detect neoplastic tissue, but to date non-invasive methods of detecting such tissue have shown only limited usefulness.

Many attempts have centered around discovering imaging agents which localize in neoplastic tissue.

There are materials such as certain porphyrins which do localize in neoplastic tissue. The porphyrins are complex tetrapyrrole compounds normally found in plants and animals. Many of these porphyrins fluoresce when exposed to an appropriate light source. One particular porphyrin preparation which selectively localizes in neoplastic tissue is hematoporphyrin derivative (HPD) prepared by treating hematoporphyrin with concentrated sulfuric acid, resulting in a crude mixture of several porphyrins. (Lipson et al J. Natl. Cancer Institute. 26:1-11, 1961) When injected into tumor bearing animals it localizes in tumors and produces a brilliant red-orange fluorescence when exposed to ultraviolet light. It has been found that dihematoporphyrin ether (DHE) (see formula I) is the active component of hematoporphyrin derivative responsible for tumor localizing properties.

Although HPD and DHE localize in neoplastic tissue and can be detected by photodynamic methods, the usefulness of these compounds is limited. This is primarily due to the fact that these photodynamic methods require invasive procedures. The HPD and DHE must be activated in situ by exposure to appropriate wavelength light. Direct observation of tissue fluorescence at best is qualitative and subjective, and varies widely between different investigators. Quenching of the fluorescence by normal tissue, body fluids, and blood is another major obstacle in achieving significant reliability and reproducibility in the use of this technique.

HPD has been radio labeled in an attempt to eliminate the major problems encountered by the photodynamic technique. Nuclear scintillation imaging procedures employing radio pharmaceuticals are simple and not invasive. Following parenteral administration of the radio labeled HPD, the radiopharmaceutical concentrates in the tumors to be detected and is imaged using appropriate nuclear medicine imaging devices. Past attempts have met with only limited success. Protoporphyrin and hematoporphyrin labeled with $^{64}Cu$ were shown to concentrate in mouse tumors in vitro but failed to achieve significant tumor uptake in vivo. Similar results were obtained with $^{57}Co$-labeled hematoporphyrin. More recent studies indicate that $^{99}Tc$ and $^{111}In$ labeled compounds localize in neoplastic tissue but have no therapeutic value.

SUMMARY OF THE INVENTION

The present invention is premised upon the realization that the following compound

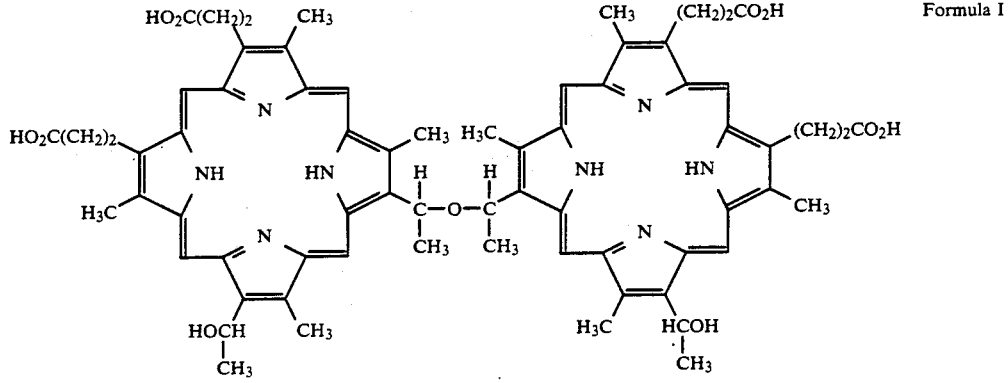

Formula I when labeled with a radionuclide at one or more of the four carboxylic acid groups or two hydroxyl groups still localizes in neoplastic tissue and can be detected by non-invasive radio scintillation imaging. Two preferred radionuclide tagged compounds are histamine and tyrosine which may be labeled with radioactive halogens such as $^{123}I$, $^{125}I$, $^{131}I$, $^{132}I$, $^{133}I$, $^{135}I$, $^{77}Br$ and $^{82}Br$ (hereafter generally referred to as radionuclide halogens).

These radiolabeled DHE compounds, when injected into a mammal, provide a means to detect neoplastic tissue. Further, when the radio labeled compound has an adequate component of particulate radiation, such as a labeled compound wherein the radionuclide is iodine 131 (a strong beta emitter) then the compound can be used as a therapeutic agent in the treatment of neoplastic tissue. The DHE localizes in the neoplastic tissue and the radiation emitted by these particular radio pharmaceuticals will act to destroy or reduce the mass of neoplastic tissue. Further advantages of the present invention will be appreciated in light of the following detailed description.

DETAILED DESCRIPTION OF THE INVENTION

Dihematoporphyrin ether (DHE) is one of several components contained in hematoporphyrin derivative (HPD). Hematoporphyrin derivative (HPD) is prepared by the method of Lipson (Lipson, R. L., et al: J. Nat. Cancer Instl. 26:1, 1961). According to this method, hematoporphyrin hydrochloride is dissolved in a mixture of 19 parts glacial acetic acid and one part concentrated sulfuric acid and allowed to stand at room temperature for 5-10 minutes. HPD is precipitated out of solution by the addition of 20 volumes of 3% sodium acetate solution. The precipitate is removed by filtration, thoroughly washed with distilled water and allowed to dry in the dark at room temperature overnight. The yield is approximately 80% HPD. HPD crystals are dissolved in normal saline and alkalis to a pH of 11.5 with 1 N NaOH. After complete dissolution, the HPD solution is quickly brought down to pH 7.4 with 1 N HCl. It is essential that the pH of the HPD solution be maintained above pH 7.4 to avoid reprecipitation. The neutralized HPD solution is sterilized by ultrafiltration techniques and packaged in a dark amber colored ampule in concentration of 5-10 mg/ml. Any form of pharmacologically acceptable buffers having a pH above 7.4 such as phosphate, citrate or bicarbonate buffer systems can be used to stabilize the HPD solution.

Dihematoporphyrin ether (DHE) is separated from the HPD solution by liquid chromotography, gel filtration or electrophoretic methods. If P-10 gel filtration is used the DHE can be recovered in the void volume. As described in Porphyrins in Phototherapy ed. A. Andrium & R. Cybeddu, Plenum Publishing Corp. (New York), 1984 pp.23-35, DHE can be separated from HPD by gel filtration using a Bio Gel P-10, 100-200 mesh packed column. (Bio Rad., Richmond, California). HPD is eluted with distilled water (pH 7-8). DHE was eluted at the exclusion limit of the column. DHE is also supplied by Johnson & Johnson under the name Photoprin II.

Radiolabeled DHE according to the present invention has the following general formula:

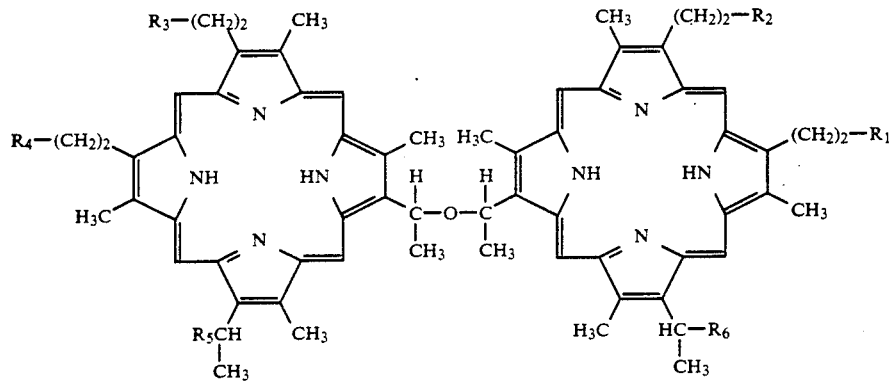

In this formula $R_1$-$R_4$ represent a carboxylic acid group (—COOH) or $C_1$-$C_{10}$ alkyl ester derivative thereof, a radio labeled amide or a radio labeled ester. $R_5$ and $R_6$ can represent hydroxyl (—OH) or the radiolabeled reaction product of a cyclic anhydride such as succinic anhydride with the hydroxyl group. This would form mono or di succinyl DHE having a carboxylic acid group which in turn can react with a radiolabeled amine or alcohol. At least one of $R_1$-$R_6$ must be radiolabeled.

Preferred radio labeled amide groups include amide groups substituted with $^{123}I$, $^{125}I$, $^{131}I$, $^{132}I$, $^{133}I$, $^{135}I$, $^{77}Br$ or $^{82}Br$. Preferably at least one of $R_1$-$R_4$ and more preferably three of the $R_1$-$R_4$ groups represent —$CO_2H$. Preferably $R_5$ and $R_6$ represents hydroxyl group. The preferred radio labeled compound is one where one of $R_1$-$R_4$ represents radio halogenated histamine or tyrosine.

According to a first method, radiolabeled DHE is prepared by reacting a radiolabeled compound or precursor with DHE under suitable reaction conditions. Preferably for us in the present invention the radiolabeled precursor will be a radiolabeled amine or radiolabeled alcohol which can form an amide or an ester with the DHE. Suitable radiolabeled amines would include imidazol substituted alkyl amines, phenol substituted alkyl amines, sulfide substituted alkyle amines. Suitable alcohols would include imidazol substituted alkyl alcohols, phenol substituted alkyl alcohols and sulfide substituted alkyl alcohols.

For example the following precursors should be suitable for use in radio labeling DHE:

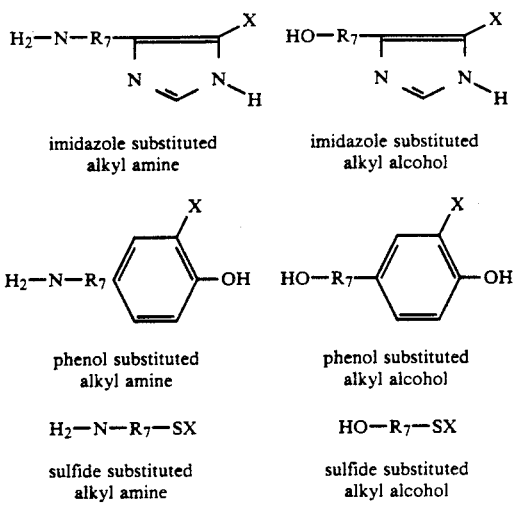

Formula II wherein $R_7$ represents $C_1$-$C_{10}$ alkylene and X represents a radionuclide halogen. Particular suitable radiolabeled amines include:

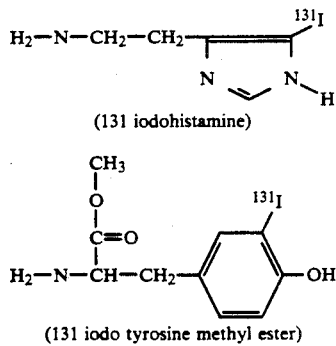

Preparation of radiolabeled precursors is well known. For example the method of radio halogenation is reported by Greenwood F. C., Hunter W. M., Glover, J. S., *The Preparation of* $^{131}$*Iodine Labeled Human*

Growth Hormone of High Specificity, Bio. Chem. Journal, vol. 89, p.114, 1963. Basically this method calls for the oxidation of, for example, sodium iodine[131] with Chlorimine T in the presence of an alkyl amine substituted with an imidazol, a phenol, or sulfide group to produce an iodine[131] radical substituted on one of the imidazol, phenol or sulfide groups. Another preferred method incorporates the use of iodogen as a oxidizing agent in place of the Chloramine T. This method is reported by Pamela J. Fraker, et al Vol. 30 Biochemical and Biophysical Research Communication pp. 849–857 (Feb. 28, 1978).

Conjugation of one of the amine radiolabeled precursors with DHE to form radiolabeled DH is carried out in an aqueous tetrahydrofuran solution in the presence of carbodiimide reagent for amide formation. Isolation and purification of the conugated products is achieved by selective precipitation and gel filtration ion exchange chromatography. Biogel P-10 is a suitable medium for gel filtration chromotography in which the aggregate of radio labeled DHE conjugates in an aqueous medium can be excluded completely from the gel while lower molecular weight radio labeling compounds such as histamine or tyrosine can be retained on the column.

Esterification of one of the alcohol precursors can be conducted by simple reaction of the alcohol with DHE in the presence of a mineral acid. Due to steric hinderance, this reaction may proceed at a relatively slow rate. Accordingly, labeling by formation of the amide is preferred.

The precursor compounds, both amines and alcohols, can also be bonded to either of the two hydroxyl groups. However, to facilitate this reaction the hydroxyl group must first be reacted with a cyclic anhydride or a diacid. The anhydride or acid react under acid pH is an aqueous medium to form an ester with a free carboxylic acid functionality. In turn, this carboxylic acid functionality can react with the amine or hydroxyl group of the precursor to form an amide or ester, respectively. Thus $R_5$ and $R_6$ can represent

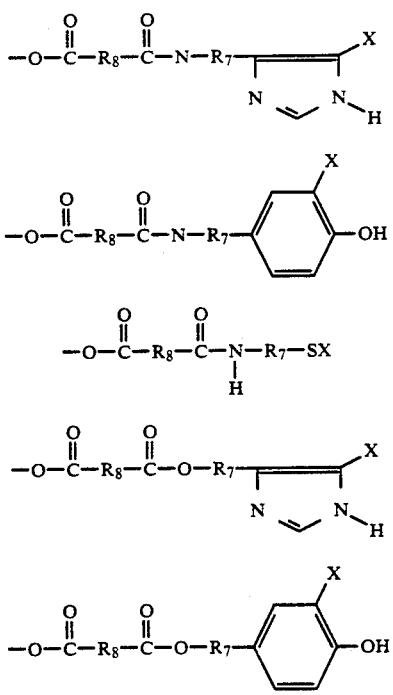

-continued

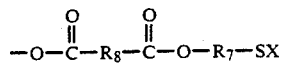

wherein $R_8$ represents $C_2$-$C_{10}$ alkylene.

The radio labeled DHE can be used for diagnostic purposes by injecting an effective amount of the radiolabeled compound and observing localization of the compound using radio scintillation methods after about 30 minutes to 72 hours (preferably about 24 hours) to allow the DHE to clear the blood. The methods of imaging using nuclear medicine imaging techniques are well known and can be conducted, for example, using a gamma camera which detects gamma radiation emitted by the radionuclide. Positron detectors can also be used with $^{77}$Br.

The administered activity will vary depending on the subject. Examples provide dose information for smaller mammals. For use in, for example, a 70 kilo human the dose range will vary from about 25 microcuries to about 2 millicuries depending on the purpose of the examination. The labeled DHE is applied parenterally and preferably intravascularly. The labeled DHE can be carried in any therapeutically acceptable carrier or vehicle such as saline.

For therapeutic uses the radio labeled DHE must have a strong component of particulate radiation, for example, a strong beta emitter. Accordingly, the radio emitting compound must be $^{125}$I, $^{131}$I, $^{132}$I, $^{133}$I, $^{135}$I, $^{82}$Br. For therapeutic applications the administered activity should be, for example, from about 500 microcuries to about 200 millicuries for a 70 kilo adult applied intravascularly. The administered activity will of course vary depending on the stage of the cancer, the age and health of the subject, and radiation dose response considerations.

The invention will be further appreciated in light of the following examples.

Example I

Preparation of Iodinated Histamine

Histamine (0.4 mg in 100 microliters of aqueous phosphate buffer) was added to an iodegen plated (4 micrograms) polypropylene test tube together with 10 microliters of Na$^{131}$I (20 millicuries). This was left at room temperature for thirty minutes. This produced an aqueous solution of 131-Iodohistamine, which can be used directly in the conjugation reaction with DHE described in Example II.

Example II

Preparation of Iodinated Histamine DHE

DHE (8.5 micromoles) was radiolabeled by coupling at least one of the four carboxylic acid groups with $^{125}$I-iodohistamine (2.13 micromoles) in 90% tetrahydrofuran (THF) in the presence of triethylamine (2.13 micromoles) and 1-ethyl-3-(3-dimethyl-aminopropyl)-carbodiimide hydrochloride (2.13 micromole) at room temperature overnight. The solvent was removed under a stream of nitrogen and the residue dissolved in 2 ml of 0.1 M NH$_4$OH. DHE was precipitated by adjusting the pH to 4 with acetic acid, washed with 0.1 M acetic acid three times and redissolved in 0.1 M NH$_4$OH. $^{125}$I-histamine DHE ($^{125}$I-hDHE) and unlabeled DHE were separated by an anion exchange column (AG1X8) by eluting the column with 20% THF, 50% THF, 90% THF, 0.1 M acetic acid and 90% THF and 0.1 M HCL and 90% THF. $^{125}$I-hDHE was eluted in the acetic acid-THF fraction. Photosensitizing activity of $^{125}$I-hDHE was confirmed by its ability to lyse red blood cells following laser radiation. Its tumor localizing ability was assessed in spontaneous memory tumor fast (SMT-F) bearing DBA/2HA mice. The following specific tumor to tissue ratio (counts per minute per gram) were obtained 24 hours after intraperataneal injection: brain (64.27), muscle (6.07), blood (3.32), lung (1.54), kidney (2.54), spleen (0.48), liver (0.15). Such ratios are similar to those obtained with $^3$H and $^{14}$C labeled HDP suggesting that biological distribution of the radiated compound is not altered by labeling procedure.

Example III

Imaging With $^{131}$I hDHE $^{131}$I hDHE was used to image tumor bearing mice. The mice were injected with 65 microcuries of $^{131}$I hDHE (20 micrograms of $^{131}$I hDHE per gram of mouse weight). After 24 hours nuclear scintillation images were obtained. The $^{131}$I hDHE localized in tumors and an image of the tumors was obtained.

Thus by labeling DHE at one of the four carboxylic acid sites or hydroxyl sites, the compound will still localize in neoplastic tissues. This in turn provides a means to identify and image neoplastic tissue and to chemotherapeutically treat malignant neoplastic tissue.

Having described our invention, we claim:

1. A method of treating neoplastic tissue in a mammal comprising parenterally applying to said mammal a effective amount of a compound having the following general formula

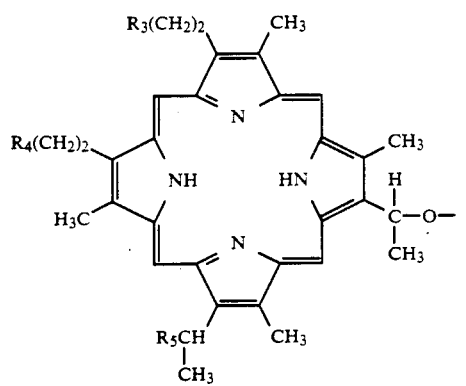

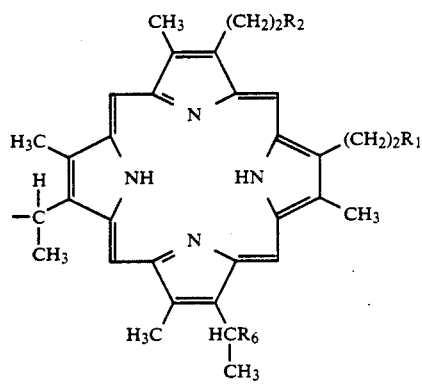

wherein $R_1$, $R_2$, $R_3$ and $R_4$ each represent —CO$_2$H or an amide or ester derivative thereof and $R_5$ and $R_6$ represent —OH or an ester derivative thereof and at least one of said $R_1$, $R_2$, $R_3$, $R_4$, $R_5$ and $R_6$ represent a radio labeled moiety having a strong component of particulate radiation, whereby said compound localizes in said neoplastic tissue wherein said radio labeled moiety includes radionuclide selected from the group consisting essentially of $^{125}$I, $^{131}$I, $^{132}$I, $^{133}$I, $^{135}$I, and $^{82}$Br.

2. The method claimed in claim 1 wherein said radionuclide is $^{131}$I.

3. The method claimed in claim 1 wherein $R_5$ and $R_6$ represent —OH said radio labeled moiety is selected from the group consisting of

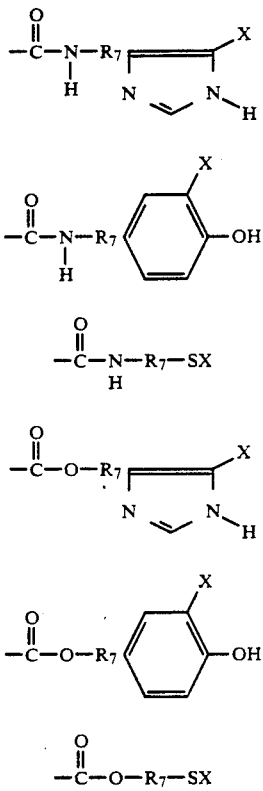

$R_7$ represents $C_1$–$C_{10}$ alkylene, wherein X represents said radionuclide.

4. The method claimed in claim 3 wherein X represents a halogen selected from the group consisting of I$^{131}$ and Br$^{82}$.

5. The method claimed in claim 1 wherein $R_5$ and $R_6$ are selected from the groups consisting of

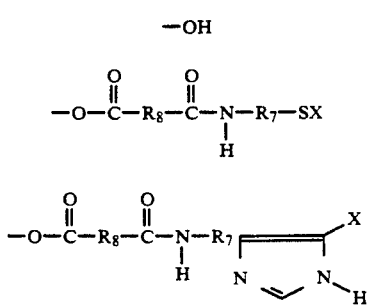

-continued
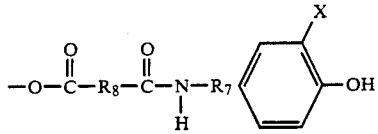
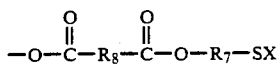
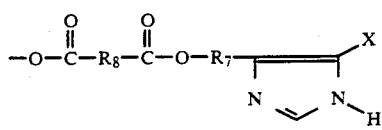
-continued
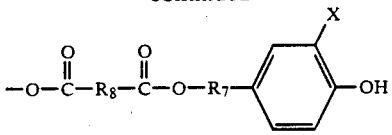
wherein $R_7$ represents $C_1$-$C_{10}$ alkylene, x represents said radionuclide and $R_8$ represents $C_2$-$C_{10}$ alkylene.
6. The method claimed in claim 1 wherein at least one of said $R_1$-$C_4$ represents a radical selected from the group consisting of
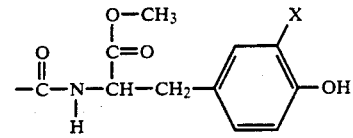
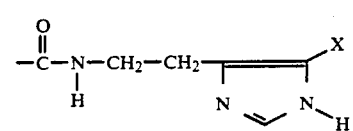
wherein X represents said radionuclide.
* * * * *